United States Patent [19]

Korthoff

[11] Patent Number: 5,051,107
[45] Date of Patent: Sep. 24, 1991

[54] SURGICAL NEEDLE-SUTURE ATTACHMENT FOR CONTROLLED SUTURE RELEASE

[75] Inventor: Herbert W. Korthoff, Westport, Conn.

[73] Assignee: United States Surgical Corporation, Norwalk, Conn.

[21] Appl. No.: 532,927

[22] Filed: Jun. 4, 1990

Related U.S. Application Data

[63] Continuation-in-part of Ser. No. 413,240, Sep. 27, 1989.

[51] Int. Cl.$^5$ .............................................. A61B 17/00
[52] U.S. Cl. ..................................... 606/224; 606/227
[58] Field of Search ............................ 606/224–227, 606/151, 231; 604/175, 165

[56] References Cited

U.S. PATENT DOCUMENTS

| | | |
|---|---|---|
| 86,769 | 2/1869 | Marriott . |
| 295,612 | 3/1884 | Bailey . |
| 299,305 | 5/1884 | Weed . |
| 877,476 | 1/1908 | Bach . |
| 1,106,667 | 8/1914 | Minahan . |
| 1,250,114 | 12/1917 | Bigelow et al. . |
| 1,558,037 | 10/1925 | Morton . |
| 1,591,021 | 7/1926 | Davis . |
| 1,613,206 | 1/1927 | Souttar .............................. 606/222 |
| 1,665,216 | 4/1928 | Morton et al. . |
| 1,678,361 | 7/1928 | Shearon . |
| 1,757,129 | 5/1930 | McClure . |
| 1,960,117 | 5/1934 | Lydeard . |
| 1,981,651 | 11/1934 | Logan . |
| 2,022,234 | 11/1935 | Everett . |
| 2,240,330 | 4/1941 | Flagg et al. ......................... 606/227 |
| 2,302,986 | 11/1942 | Vollrath . |
| 2,411,079 | 11/1946 | Baule . |
| 2,802,468 | 8/1957 | Everett . |
| 2,814,296 | 11/1957 | Everett . |
| 2,910,983 | 11/1959 | Everett . |
| 2,928,395 | 3/1960 | Forbes et al. . |
| 3,311,110 | 3/1967 | Singerman et al. . |
| 3,394,704 | 7/1968 | Dery . |
| 3,416,534 | 12/1968 | Quinn . |
| 3,799,169 | 3/1974 | Beroff et al. . |
| 3,835,912 | 9/1974 | Kristensen et al. . |
| 3,875,946 | 4/1975 | Duncan . |
| 3,880,167 | 4/1975 | Hardwick . |
| 3,890,975 | 6/1975 | McGregor . |
| 3,898,369 | 8/1975 | Clabburn .......................... 428/34.9 |
| 3,910,282 | 10/1975 | Messer et al. . |
| 3,918,455 | 11/1975 | Coplan ................................ 606/225 |
| 3,924,630 | 12/1975 | Walldorg . |
| 3,926,194 | 12/1975 | Greenberg et al. . |
| 3,943,933 | 3/1976 | Gertzman . |
| 3,949,756 | 4/1976 | Ace . |
| 3,963,031 | 6/1976 | Hunter ................................ 606/227 |
| 3,980,177 | 9/1976 | McGregor ......................... 606/227 |
| 3,981,307 | 9/1976 | Borysko . |
| 4,054,144 | 10/1977 | Hoffman et al. . |
| 4,072,041 | 2/1978 | Hoffman et al. . |
| 4,124,027 | 11/1978 | Boss . |
| 4,127,133 | 11/1978 | Martinez . |
| 4,169,477 | 10/1979 | Bokros . |
| 4,359,053 | 11/1982 | Benjamin . |
| 4,411,654 | 10/1983 | Boarini et al. ...................... 604/165 |
| 4,596,728 | 6/1986 | Yang et al. . |
| 4,624,879 | 11/1986 | Van Dijck et al. . |
| 4,650,703 | 3/1987 | Kleinheins ......................... 428/34.9 |
| 4,672,734 | 6/1987 | Kawada et al. . |
| 4,792,336 | 12/1988 | Hlavaceh et al. .................... 623/13 |
| 4,803,103 | 2/1989 | Pithouse et al. .................. 428/35.1 |
| 4,804,733 | 2/1989 | Bataille ............................. 428/35.1 |
| 4,805,292 | 2/1989 | Noguchi ............................. 27/445 |

FOREIGN PATENT DOCUMENTS 0358451  3/1990  European Pat. Off. .
2432861  ,1/1974  France .

OTHER PUBLICATIONS

Raychem Corporation Product specification RT-850 for Thermofit ™ Kynar Tubing dated Mar. 6, 1984.

Primary Examiner—Max Hindenburg
Assistant Examiner—Gary Jackson
Attorney, Agent, or Firm—Thomas R. Bremer; Peter G. Dilworth; Rocco S. Barrese

[57] ABSTRACT

A combined surgical needle-suture device of controlled suture release characteristics and a method for manufacturing the device employ a shrinkable tubing to connect the needle to the suture. A tensioning force is applied to the device to bring the average force required for the release of the needle from its attached suture to within a predetermined range of average pull-out force.

29 Claims, 4 Drawing Sheets

SURGICAL NEEDLE-SUTURE ATTACHMENT FOR CONTROLLED SUTURE RELEASE

CROSS REFERENCE TO RELATED APPLICATION

This application is a continuation-in-part of commonly assigned, copending U.S. patent application Ser. No. 413,240, filed Sept. 27, 1989.

BACKGROUND OF THE INVENTION

The present invention relates to a method for attaching a surgical needle to a suture to provide a combined surgical needle-suture device possessing controlled suture release characteristics and, more particularly, to such a method in which a shrinkable tubing is employed to secure the needle to the suture.

For many years, surgeons have employed needle-suture combinations in which a suture or ligature is attached to the shank end of a needle. Such needle-suture combinations are provided for a wide variety of monofilament and braided suture materials, both absorbable and non-absorbable, e.g., catgut, silk, nylon, polyester, polypropylene, linen, cotton, and absorbable synthetic materials such as polymers and copolymers of glycolic and lactic acids.

Needle-suture combinations fall into two general classes: standard needle attachment and removable or detachable needle attachment. In the case of standard needle attachment, the suture is securely attached to the needle and is not intended to be separable therefrom, except by cutting or severing the suture. Removable needle attachment, by contrast, is such that the needle is separable from the suture in response to a force exerted by the surgeon. Minimum acceptable forces required to separate a needle from a suture (for various suture sizes) are set forth in the *United States Pharmacopoeia* (USP). The *United States Pharmacopoeia* prescribes minimum individual pull-out forces and minimum average pull-out forces as measured for five needle-suture combinations. The minimum pull-out forces for both standard and removable needle-suture attachment set forth in the *United States Pharmacopoeia* are hereby incorporated by reference.

One typical method for securing a suture to a needle involves providing a cylindrical recess in the shank end of a needle and securing a suture therein. For example, U.S. Pat. No. 1,558,037 teaches the addition of a cement material to such a substantially cylindrical recess to secure the suture therein. Additional methods for bonding a suture within a needle bore are described in U.S. Pat. Nos. 2,928,395 (adhesives) and 3,394,704 (bonding agents). Alternatively, a suture may be secured within an axial bore in a needle by swaging the needle in the region of the recess. See, e.g., U.S. Pat. No. 1,250,114. Additional prior art methods for securing a suture within a needle bore include expansion of a catgut suture through the application of heat (U.S. Pat. No. 1,665,216), inclusion of protruding teeth within the axial bore to grasp an inserted suture (U.S. Pat. No. 1,678,361) and knotting the end of the suture to be inserted within the bore to secure the suture therein (U.S. Pat. No. 1,757,129).

Methods for detachably securing a suture to a needle are also well known. For example, U.S. Pat. Nos. 3,890,975 and 3,980,177 teach swaging a suture within a needle bore such that the suture has a pull-out valve of 3 to 26 ounces. Alternative detachable attachment methods include providing a weakened suture segment (U.S. Pat. No. 3,949,756), lubricant tipping the end of a suture to be inserted in the axial bore of a needle (U.S. Pat. No. 3,963,031) and pre-tensioning a suture that is swaged within an axial needle bore (U.S. Pat. No. 3,875,946). See also, U.S. Pat. Nos. 3,799,169; 3,880,167; 3,924,630; 3,926,194; 3,943,933; 3,981,307; 4,124,027; and, 4,127,133.

Another method for attaching a suture to a needle involves the use of tubing which is secured to the shank end of the needle and to the suture. For example U.S. Pat. No. 1,613,206 describes the use of a tubing (preferably silver) which is secured to the shank end of a needle and to a ligature. It is suggested that the tube may be attached to the needle by pressure or soldering and to the ligature by pressure or cementing. It is also suggested that the shank of the needle be of reduced cross section and that the furthest extremity of the reduced diameter shank section be provided with a spike or point upon which the suture may be secured prior to tube application.

U.S. Pat. No. 2,240,330 describes a tubing attachment method whereby the tubing and suture are releasably secured to the needle. In particular, the needle and tubing are provided with cooperating catch and abutment means which are released one from the other by rotating the needle 90° relative to the tubing (or vice versa). The tubing is manufactured from spring-tempered carbon steel or chrome nickel steel and is secured to the suture by heating the tubing and then swaging to the suture.

U.S Pat. No. 3,311,100 relates to a flexible composite suture having a tandem linkage. The needle is secured to a flexible suture leader manufactured from a readily sterilizable plastic such as nylon, linear polyethylene, isotactic polypropylene, polyester, silk or other proteinaceous material, e.g., by inserting and crimping the leader within an axial bore in the needle shank. The opposite end of the suture leader is crimped within a connector sleeve of a thin walled metal tubing, e.g., stainless steel. The opposite end of the tubing is crimped around a stiff suture, e.g., monofilament stainless steel.

U.S. Pat. No. 3,918,455 describes a needle-suture attachment wherein a hollow suture portion is secured to the shank end of a needle which is of reduced cross-section as compared to the remainder of the needle.

Additional patents which describe the use of tubing to effect suture-needle attachment include U.S. Pat. Nos. 4,672,734 (forming needle from U-shaped metal plate around suture); 4,359,053 (silicone tubing); 3,835,912 (laser welding of metal tube to needle); 2,814,296; 2,802,468 (chamfered tubing ends); 2,302,986; 2,240,330; 1,981,651 (needle and tubing screw threaded); 1,960,117; and 1,591,021.

Numerous disadvantages exist with methods used heretofore to effect needle-suture attachment. For example, those methods which involve the formation and use of an axial bore in the shank end of the needle require the use of expensive hole forming equipment. Moreover, it is difficult to maintain the bore concentric with the center-line of the needle and to control the depth (and diameter) of the bore when drilling the needle shank, whether using conventional drilling equipment or laser drilling. Another disadvantage is the possibility that foreign substances may inadvertently or uncontrollably be introduced into the needle bore, e.g., oil used during drilling or silicone from the needle silconization process. Safeguards employed in an attempt to prevent the introduction of such foreign materials, e.g., water blocking during needle siliconization, are inconvenient adding time, effort and cost to the needle production process.

Attachment processes which employ bored needle shanks also limit the range of materials from which needles may be fabricated in a cost effective fashion. For example, it is exceedingly difficult to drill Series 300 stainless steel (laser drilling is required) and, once drilled it is difficult to swage Series 300 stainless steel in a consistent and reliable manner. For this reason, Series 300 stainless steel is not employed for the vast majority of needled suture products despite its advantageous combination of strength and ductility characteristics as compared to conventionally employed Series 400 stainless steel.

Additional disadvantages associated with needle-suture attachment methods which employ bored needle shanks include the weakness imparted to the bored section of the needle, particularly after swaging, and the attendant increased possibility that the needle will fracture in this region. It is also difficult to provide a specialized surface finish to the needle shank to assist in needle attachment, e.g., a texturized surface and/or a tapered bore. Swaging equipment used in such needle-suture attachment methods is also maintenance intensive.

Needle-suture attachment methods which have employed tubings heretofore also exhibit numerous disadvantages. Methods which employ metal tubings greatly diminish the flexibility of the needle-suture combination in the attachment region Such diminished flexibility has a deleterious effect in many surgical procedures. Swaging of the tubing to the needle and the suture is also undesirable in that swaging is time-consuming, maintenance intensive, and subject to variability in attachment force.

Moreover, needle-suture attachment methods which have employed tubings heretofore have necessarily required the use of tubing having an inner diameter essentially equal to the outer diameters of the needle shank and suture tip to be attached. Too large a difference between the aforesaid inner and outer diameters inhibits the attachment process, and prevents a tight, secure interface between needle (and/or suture) and tubing. The limited tolerance between the tubing inner diameter and the needle shank/suture outer diameters in such methods make these dimensions critical, thereby making the attachment process more difficult and time-consuming, and increasing the likelihood of attachment failure and/or rejected materials.

Commonly assigned, copending U.S. patent application Ser. No. 413,240, filed Sept. 27, 1989, of which the present application is a continuation-in-part describes and claims a combined surgical needle-suture device and surgical needle-suture attachment method which overcomes the aforementioned drawbacks of the previously known needle-suture combinations and needle-suture attachment methods. In accordance with said application, a combined surgical needle-suture device is provided in which a surgical needle having a shank of reduced cross-section is attached to a suture through a shrinkable tubing, or microferrule, which is fitted about the needle shank and a portion of the suture. Application of energy to the shrinkable tubing brings the tubing into engagement with both the needle shank and the suture. The physical and chemical characteristics of the shrinkable tubing material, the relative diameters of the tubing, the needle shank and the suture, and the amount of energy applied to the tubing may be controlled to provide a needle-suture combination having a desired pull-out force. It is thus possible to produce standard needle-suture combinations and removable needle-suture combinations using a single attachment process and a common inventory of materials.

Minimum average pull-out forces for various sizes of combined surgical needle-suture devices are set forth in the *United States Pharmacopoeia* and are as follows:

| Suture Size | Average Pull-Out Force/Ounces |
|---|---|
| 8/0 | 2.39 |
| 7/0 | 3.20 |
| 6/0 | 5.92 |
| 5/0 | 7.97 |
| 4/0 | 15.97 |
| 3/0 | 23.63 |
| 2/0 | 38.80 |
| 1/0 | 52.89 |
| 1 | 63.48 |
| 2 and larger | 63.48 |

U.S. Pat. No. 3,875,946, referred to supra, the contents of which are incorporated by reference herein, describes needle-suture combinations said to exhibit suture pull-out values that are substantially less than those given by the *United States Pharmacopoeia* as set forth above. According to U.S. Pat. No. 3,875,946, employing the procedure described therein, combined surgical needle-suture devices can be obtained with the following average pull out forces:

| Suture Size | Average Pull-Out Force/Ounces |
|---|---|
| 8/0 | 1-2 |
| 7/0 | 1-3 |
| 6/0 | 2-5 |
| 5/0 | 3-7 |
| 4/0 | 3-15 |
| 3/0 | 3-23 |
| 2/0 | 3-26 |
| 1/0 | 10-26 |
| 1 | 10-26 |
| 2 and larger | 10-26 |

These pull-out forces are obtained by prestressing the suture, i.e., by applying tension to the suture after the tip of the suture has been inserted into an axial bore, or recess, formed in the blunt end of the needle and the needled suture has been swaged so that the force required to pull the suture out of the needle access exceeds the minimum limits on needle attachment set forth in the *United States Pharmacopoeia* but is less than the actual tensile strength of the suture used. As the suture is pulled from the needle during application of the tensioning force, the force required to move the suture relative to the swaged section decreases. When the tensioning force required to move the end of the suture relative to the needle barrel drops to the desired pull-out value, the tension is released.

The foregoing procedure is said to permit better control of the resulting needle-suture device in that the force required to separate a suture of a particular size from its attached needle is uniform.

SUMMARY OF THE INVENTION

In accordance with the present invention, there is provided a method for attaching a surgical needle to a suture to provide a combined surgical needle-suture device exhibiting a predetermined range of average pull-out force for a suture of given size which comprises:

(a) providing a needle having a shank end of reduced cross-section;

(b) placing a shrinkable tubing around the reduced diameter shank and the suture;

(c) applying energy to the shrinkable tubing to bring the tubing into engagement with the needle shank and suture;

(d) prestressing the suture with respect to the needle by applying sufficient tension to the suture to move it relative to the needle; and, (e) releasing the tension when the pull-out force drops to an average value within a predetermined range.

In addition to the foregoing surgical needle-suture attachment method, the present invention includes the resulting combined surgical needle-suture device.

BRIEF DESCRIPTION OF THE DRAWINGS

The present invention will become more apparent from the following detailed description taken in conjunction with the accompanying drawings in which.

DETAILED DESCRIPTION OF THE INVENTION

The present invention relates to a combined surgical needle-suture method and resulting surgical needle-suture device featuring controlled suture release. The invention has application to any suture material whether absorbable or non-absorbable, natural or synthetic, braided or monofilament, and to any needle material and configuration whether straight or curved. For example, the suture can be a non-absorbable material selected from the group consisting of silk, nylon, polyester, polypropylene, linen and cotton. The suture can be an absorbable material selected from the group consisting of gut and synthetic materials including polymers and copolymers of glycolic and lactic acids. The suture can be a monofilament or a braided multifilament.

Figure 1:
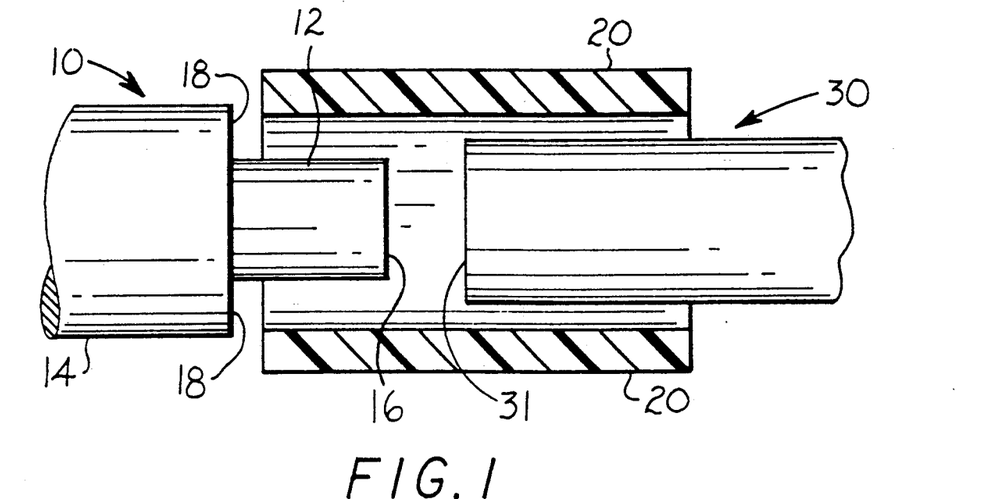
FIG. 1 is a side cross-sectional view of a needle and a suture with a tubing positioned therearound (prior to engagement of the tubing with the needle and suture)
Figure 2:
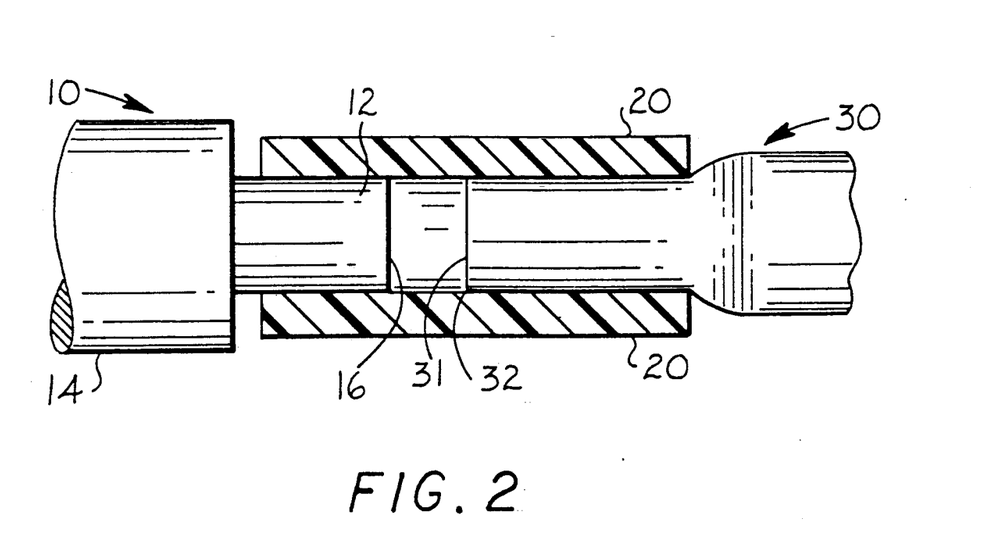
FIGS. 2 and 3 are side cross-sectional views of the tubing of FIG. 1 in engagement with the needle and suture and showing the positioning of the suture tip prior to (FIG. 2) and following (FIG. 3) application of tensioning force to the suture.
Figure 3:
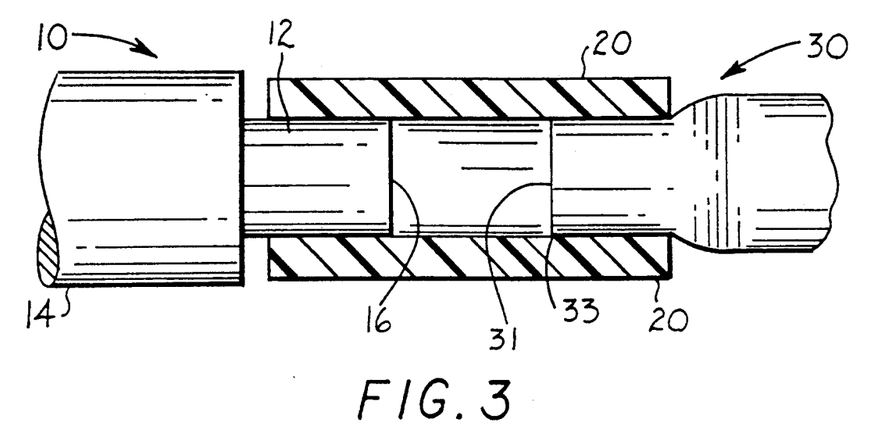
Figure 5:
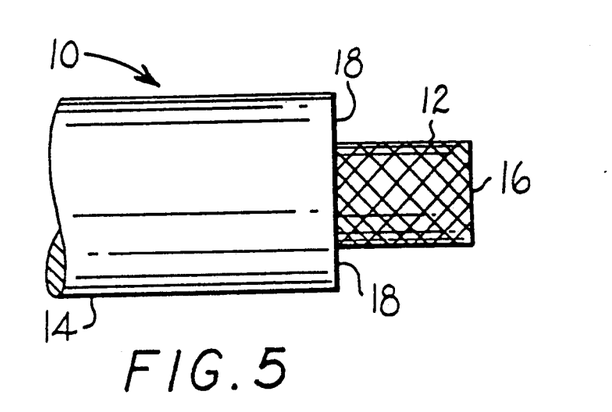
FIG. 5 is a side view of an alternative embodiment of the present invention in which a shank of the needle is scored.
Figure 6:
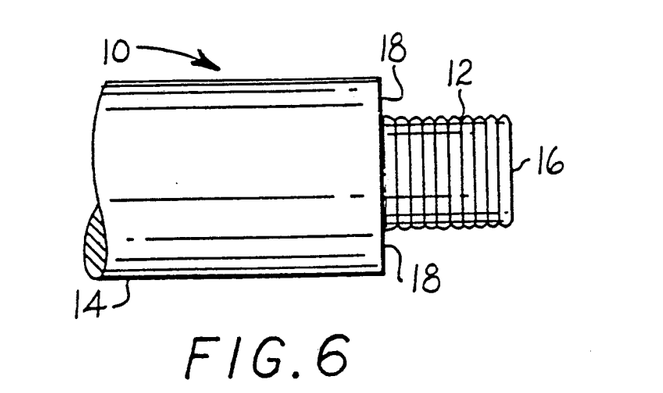
FIG. 6 is a side view of an alternative embodiment of the present invention in which the needle shank is ribbed.
Figure 7:
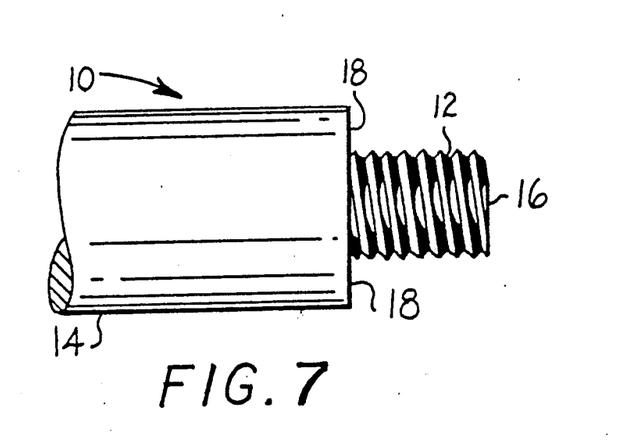
FIG. 7 is a side view of an alternative embodiment of the present invention in which the needle shank is threaded.
Figure 8:
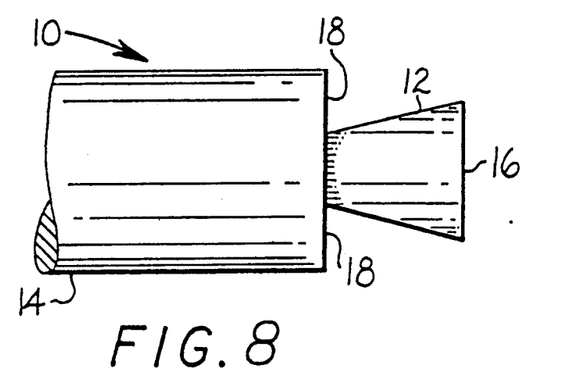
FIG. 8 is a side view of an alternative embodiment of the present invention in which the needle shank is tapered to expand in a direction away from a remainder of the needle.
Figure 9:
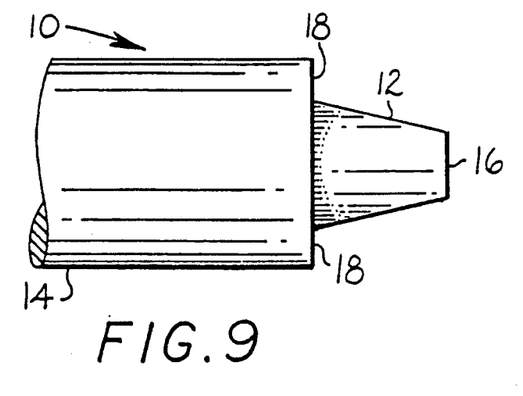
FIG. 9 is a side view of an alternative embodiment of the present invention in which the needle shank is tapered to expand in a direction towards the remainder of the needle.

Referring to FIGS. 1-3, needle 10 has a reduced cross-sectional diameter at its shank end 12 relative to the remainder of the needle 14. The diameter of shank end 12 may be reduced by any conventional means, e.g., by machining on a lathe. Typically, shank end 12 has a diameter from 10 to 65% smaller than the remaining portion 14 of the needle, and preferably from 25 to 50% smaller. It is also possible to provide shank end 12 with a texturized surface to facilitate gripping by shrinkable tubing 20. For example, shank end 12 may be scored, ribbed or threaded, in whole or in part (FIGS. 5-7 respectively). It may also be desirable to taper shank end 12 such that its butt, or distal, end 16 is of greater cross-sectional diameter than the cross-sectional diameter of shank end 12 in the region of shoulder 18, or vice versa (FIGS. 8 and 9 respectively). Shank end 12 is placed within tubing 20 as shown in FIG. 1.

Suture 30 is also positioned within shrinkable tubing 20 with suture tip 31 abutting or separated a short distance from distal end 16 of shank 12. As shown in FIG. 1, suture 30 may initially be of uniform cross-section throughout its length. Alternatively, the tip region of suture 30, i.e., the region inserted into tubing 20, may be of reduced cross-section relative to the remainder of suture 30, e.g., by tipping the suture tip with an adhesive or resinous tipping agent while suture 30 is under tension. (See, e.g., Canadian Patent No. 1,009,532). Resin tipping may be desirable to prevent brooming of the suture, particularly for multifilament braided sutures, by rigidifying the end of the suture thus facilitating its handling during the attachment process. Reducing the diameter of the suture tip, as by tipping under tension, may be desirable to allow a suture of larger diameter, e.g., a suture diameter equal to the diameter of the needle to which it is to be attached, to be more efficiently attached to the needle using the shrinkable tubing of the present invention. It is not necessary according to the present invention, however, to reduce the diameter of the tip region of suture 30 to efficiently attach needle 10 to suture 30. Indeed, it may be possible or desirable to apply a tipping agent to prevent brooming without reducing suture diameter. As shown in FIG. 1, shrinkable tubing 20 initially has an inner diameter that is larger than the outer diameter of the tip region of suture 30, thereby minimizing the importance of suture tipping.

After shrinkable tubing 20 is placed around shank end 12 of needle 10 and the tip region of suture 30, energy is applied to tubing 20. In response to this energy, tubing 20 contracts or shrinks and engages shank end 12 and suture 30. The overall length of tubing 20 may also be affected by the application of energy, e.g., the length of tubing 20 may reduce. Thus, the shrinking of tubing 20 brings the inner surface of tubing 20 into engagement with shank end 12 and suture 30, thereby securing suture 30 to needle 10. Suitable energy sources include heat (convective or conductive), radiation, microwave energy, etc.

As shown in FIGS. 1-2, shrinkable tubing 20 is simultaneously placed around both suture 30 and shank end 12 of needle 10 in one embodiment of the present invention. It is preferable, however, to sequentially secure tubing 20 to needle 10 and suture 30. Thus, in a preferred embodiment of the present invention, shrinkable tubing 20 is initially secured to shank end 12 through the localized application of energy to tubing 20 in the region surrounding shank end 12. After tubing 20 has been brought into engagement with shank end 12, suture 30 is inserted into tubing 20 and additional energy is applied thereto. Sequential shrinkage of tubing 20 makes it possible to vary the amount of energy used in securing tubing 20 to shank end 12 and suture 30, respectively, and to limit the exposure of suture 30 to energy during the attachment process. It may also be desirable to cool suture 30 in the region outside tubing 20 to prevent any undesirable degradation thereof, e.g., with a cold air curtain.

Figure 4:
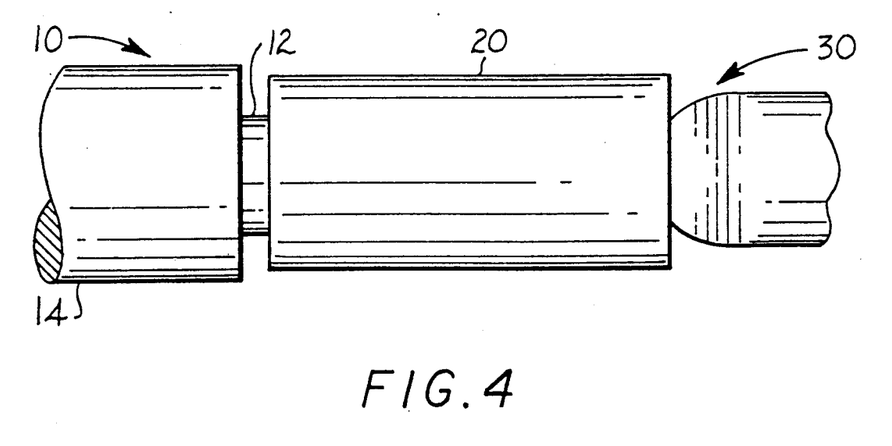
FIG. 4 is a side view of the combined surgical needle-suture device of FIG. 3.

As shown in FIGS. 2-4, the shrinkage of tubing 20 typically compresses suture 30 to some extent. This is particularly true where the suture is a braided, multifilament material having void spaces in its structure. For example, tubing 20 may compress suture 30 by as much as 30 to 35% for a braided, synthetic absorbable suture and by a minimal amount for a relatively stiff material such as a monofilament surgical gut.

Shrinkable tubing 20 may be manufactured from any material which shrinks, i.e., reduces in diameter, in response to the application of energy. Suitable materials include "memory metals," e.g., nickel-titanium mixtures, nickel-iron-titanium mixtures, or copper based materials, as are well known in the art (see, e.g. U.S. Pat. Nos. 3,759,552; 3,801,954; 4,198,081; and 4,773,680), and shrinkable plastic materials, such as polyvinylidene fluoride materials available from Raychem Corporation, Menlo Park, Calif., under the tradename Kynar. In the case of shrinkable plastic materials, the tubing is typically extruded such that the inner diameter is less than the final desired inner diameter, i.e., the inner diameter of the tubing after energy application in the attachment method of the present invention. Thereafter, the extruded tubing is expanded radially outward through radial expansion means to provide a tubing of expanded inner diameter as shown, for example, by tubing 20 in FIG. 1. Such plastic tubing is thus adapted to shrink or "recover" to its original extruded inner diameter in response to the application of a predetermined amount of energy.

The amount of energy applied to the tubing to effect the desired attachment, i.e., diameter reduction, depends upon the chemical characteristics of the tubing material, the relative dimensions of the tubing, the shank end of the needle and the suture, and the desired pull-out force for the needle-suture combination. For example, one polyvinylidene fluoride material available from Raychem Corporation (RT-850) shrinks at temperatures greater than 175° C., and is adapted to recover to about 50% of its radially expanded inner diameter. In such case, tubing 20 may be brought into engagement with shank end 12 of needle 10 and suture 30, either simultaneously or sequentially, by heating tubing 20 to a temperature above 175° C. Tubing 20 may be heated through contact with a hot gas stream or with heated dies, or by other heating means. Typically, the outer diameters of shank end 12 and suture 30 (in the region inserted into tubing 20) are greater than the fully recovered diameter of tubing 20, e.g., greater than 50% of the initial inner diameter of tubing 20 for the RT-850 material, such that tubing 20 engages shank end 12 and suture 30. It is preferred that the attachment conditions be controlled such that the tubing remains secured to the needle once the suture is detached.

The foregoing surgical needle-suture attachment procedure has many advantages over previous attachment methods. Machining of the needle to provide a reduced diameter needle shank is much easier and more controllable than drilling processes, and permits the use of needle alloys which have previously been impractical, e.g., Series 300 stainless steel and MP35N (available from SPS Technologies). These heretofore impractical alloys have advantageous strength and ductility characteristics as compared to conventionally used Series 400 stainless steels. Moreover, an unreliable, expensive and maintenance intensive swaging process is replaced by a sterile, controllable and relatively inexpensive energy supply. The tubing used in the present invention may be color coded to designate suture material, standard versus detachable attachment, etc., particularly where a plastic tubing is employed.

The attachment method is also much more efficient from a processing and inventory control standpoint. For example, the tubing may be removed from a needle and the needle attached to a fresh suture, e.g., in instances where the suture and/or attachment properties of the initial suture-needle combination are outside specifications. In many instances, the suture may also be recovered and reused, thereby greatly reducing processing waste. The range of acceptable suture diameters is greatly expanded due to the ability of the tubing to recover or shrink to varying degrees, thereby minimizing the likelihood that suture production will be rejected for inability to attach several needle sizes because the shrinkable tubing is capable of recovering or shrinking to varying degrees. This greatly simplifies inventory considerations. Moreover, the needle-suture combinations are atraumatic and advantageously exhibit flexibility in the attachment region.

The pull-out characteristics which characterize the combined surgical needle-suture device of the present invention are obtained by prestressing the suture relative to the needle, i.e. by applying a tension or pulling force to the suture after following the step of thermally shrinking the tubular connector on the needle shank and suture to effect their attachment. As the suture is pulled from the needle, the force required to move the suture relative to the tubular attachment, or microferrule, decreases. When the force required to move the end of the suture relative to the needle drops to the desired pull-out value, the tension is released.

During the suturing operation, the needle remains attached to the suture. However, at any desired time, the needle can easily be removed from the suture by simply pulling on the needle with a force of from 1 to about 26 ounces depending upon the suture size.

Combined surgical needle-suture devices having the pull-out values set forth below can be manufactured by applying sufficient tension to the suture to move it relative to the tubular attachment, and then releasing the tension when the force drops to within the following range for that size of suture. For example, the range of average pull-out force for a variety of suture sizes can advantageously be as follows:

| Suture Size | Average Pull-Out Force/Ounces |
| --- | --- |
| 8/0 | 1-2 |
| 7/0 | 1-3 |

| Suture Size | Average Pull-Out Force/Ounces |
| --- | --- |
| 6/0 | 2-5 |
| 5/0 | 3-7 |
| 4/0 | 3-15 |
| 3/0 | 3-23 |
| 2/0 | 3-26 |
| 1/0 | 10-26 |
| 1 | 10-26 |
| 2 and larger | 10-26 |

Comparing FIGS. 2 and 3, it will be seen that prior to tensioning, tip 31 of suture 30 is positioned with respect to point 32 along the length of tubing 20 and following tensioning, tip 31 of suture 30 has been moved some distance away from point 32 to a new point 33. The distance between points 32 and 33 can vary provided the average pull-out force required for needle separation falls within the values indicated above. In general, this distance can vary from about 30 to about 50, and preferably from about 35 to about 45 percent of the length of tubing 20 which comes into contact with the surface of shank 12.

Prestressing the suture can be accomplished, e.g., by employing the apparatus and technique described in aforementioned U.S. Pat. No. 3,875,946.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A method for attaching a surgical needle to a suture to provide a combined surgical needle-suture device exhibiting a predetermined range of average pull-out force for a suture of given size which comprises:
   (a) providing a needle having a shank end of reduced cross-section;
   (b) placing a shrinkable tubing around the reduced diameter shank and the suture;
   (c) applying energy to the shrinkable tubing to bring the tubing into engagement with the needle shank and suture to couple the same without crimping or swaging;
   (d) prestressing the suture with respect to the needle by applying sufficient tension to the suture to move it relative to the needle; and,
   (e) releasing the tension when the pull-out force drops to an average value within a predetermined range.

2. The method of claim 1 wherein the average value of pull-out force for a particular size of suture is as follows:

| Suture Size | Average Pull-Out Force/Ounces |
| --- | --- |
| 8/0 | 1-2 |
| 7/0 | 1-3 |
| 6/0 | 2-5 |
| 5/0 | 3-7 |
| 4/0 | 3-15 |
| 3/0 | 3-23 |
| 2/0 | 3-26 |
| 1/0 | 10-26 |
| 1 | 10-26 |
| 2 and larger | 10-26 |

3. The method of claim 1 wherein prestressing results in displacement of the suture a distance from an initial point along the length of the tubing which is in contact with the shank, the distance representing from about 30 to about 50 percent of the total length of the tubing in contact with the shank.

4. The method of claim 1 wherein prestressing results in displacement of the suture a distance from an initial point along the length of the tubing which is in contact with the shank, the distance representing from about 35 to about 45 percent of the total length of the tubing in contact with the shank.

5. The method of claim 1, wherein said shrinkable tubing is simultaneously placed around the reduced diameter shank and the suture.

6. The method of claim 1 wherein the shrinkable tubing is first placed around the reduced diameter shank and brought into engagement therewith by applying the energy to the shrinkable tubing, and
   then the shrinkable tubing is placed around the suture and brought into engagement therewith by applying the energy to the shrinkable tubing.

7. The method of claim 1 additionally comprising
   cooling the suture in a region outside the shrinkable tubing to prevent any undesirable degradation thereof.

8. The method of claim 1 additionally comprising
   extruding the shrinkable tubing such that an inner diameter thereof is less than an inner diameter of the shrinkable tubing after energy application, and
   expanding the extruded shrinkable tubing radially outwardly to provide the tubing with an expanded inner diameter, such that the shrinkable tubing is adapted to recover its extruded inner diameter in response to the subsequent energy application.

9. A combined surgical needle-suture device which comprises:
   (a) a needle having a shank of reduced cross-section;
   (b) a suture; and,
   (c) a shrinkable tubing around said needle shank and a portion of said suture to couple the same without crimping or swaging;
   the suture being pre-stressed with respect to the needle so that the suture is displaced a distance from an initial point along the length of the tubing which is in contact with the shank whereby the suture may be separated from the needle by a pull-out force which is within a predetermined range.

10. The combined surgical needle-suture device of claim 9 wherein the predetermined range of pull-out force for a particular size of suture is as follows:

| Suture Size | Average Pull-Out Force/Ounces |
| --- | --- |
| 8/0 | 1-2 |
| 7/0 | 1-3 |
| 6/0 | 2-5 |
| 5/0 | 3-7 |
| 4/0 | 3-15 |
| 3/0 | 3-23 |
| 2/0 | 3-26 |
| 1/0 | 10-26 |
| 2 and larger | 10-26 |

-continued

| Suture Size | Average Pull-Out Force/Ounces |
| --- | --- |
| 1 | 10-26 |
| 2 and larger | 10-26 |

11. The combined surgical needle-suture device of claim 10 wherein said suture is a braided multifilament.

12. The combined surgical needle-suture device of claim 9 wherein the distance is from about 30 to about 50 percent of the total length of the tubing in contact with the shank.

13. The combined surgical needle-suture device of claim 9 wherein the distance is from about 35 to about 45 percent of the total length of the tubing in contact with the shank.

14. The combined surgical needle-suture device of claim 9 wherein said suture is a non-absorbable material selected from the group consisting of silk, nylon, polyester, polypropylene, linen and cotton.

15. The combined surgical needle-suture device of claim 9 wherein said suture is a braided multifilament.

16. The combined surgical needle-suture device of claim 15 wherein said shrinkable tubing compresses said suture by about 30-35 percent.

17. The combined surgical needle-suture device of claim 9 wherein said suture is a monofilament.

18. The combined surgical needle-suture device of claim 9 wherein said suture is an absorbable material selected from the group consisting of gut and synthetic materials including polymers and copolymers of glycolic and lactic acids.

19. The combined surgical needle-suture device of claim 9 wherein said suture portion is tipped with an adhesive or resinous coating.

20. The combined surgical needle-suture device of claim 9 wherein said shrinkable tubing is manufactured from a memory metal or a shrinkable plastic material.

21. The combined surgical needle-suture device of claim 20 wherein said shrinkable plastic material is a polyvinylidene fluoride material.

22. The combined surgical needle-suture device of claim 5 wherein said needle shank is boreless.

23. The combined surgical needle-suture device of claim 5 wherein an end of said needle shank has a diameter about 10-65 percent smaller than a remainder of said needle.

24. The combined surgical needle-suture device of claim 23 wherein the diameter of said end of said needle shank is about 25-50 percent smaller than the remainder of said needle.

25. The combined surgical needle-suture device of claim 5 wherein said shank of reduced cross-section forms a shoulder with a remainder of said needle.

26. The combined surgical needle-suture device of claim 25 wherein said shank of reduced cross-section is tapered to expand in a direction away from said shoulder, such that a distal end of said shank is of greater cross-sectional diameter than cross-sectional diameter of said shank in a region of said shoulder.

27. The combined surgical needle-suture device of claim 25 wherein said shank of reduced cross-section is tapered to expand in a direction towards said shoulder, such that a distal end of said shank is of smaller cross-sectional diameter than cross-sectional diameter of said shank in a region of said shoulder.

28. The combined surgical needle-suture device of claim 5 wherein said shank is provided with a texturized surface to facilitate gripping by said shrinkable tubing.

29. The combined surgical needle-suture device of claim 28 wherein said shank is scored, ribbed or threaded in whole or in part.

* * * * *